United States Patent [19]
Swain et al.

[11] Patent Number: 6,157,038
[45] Date of Patent: Dec. 5, 2000

[54] MOUNTING ELECTROSTATOGRAPHIC END FLANGE

[75] Inventors: Eugene A. Swain; John J. Darcy, III, both of Webster, N.Y.

[73] Assignee: Xerox Corporation, Stamford, Conn.

[21] Appl. No.: 09/210,186

[22] Filed: Dec. 11, 1998

[51] Int. Cl.[7] .................................................. G01N 21/64
[52] U.S. Cl. ........................................ 250/459.1; 250/302
[58] Field of Search .................................. 250/302, 459.1

[56] References Cited

U.S. PATENT DOCUMENTS

| | | | |
|---|---|---|---|
| 4,455,810 | 6/1984 | Kreager et al. ............................. | 53/451 |
| 4,561,763 | 12/1985 | Basch . | |
| 5,331,171 | 7/1994 | Bongi ................................... | 250/461.1 |
| 5,357,321 | 10/1994 | Stenzel et al. . | |
| 5,453,625 | 9/1995 | Lawson et al. ....................... | 250/459.1 |
| 5,521,678 | 5/1996 | Riehle et al. . | |
| 5,666,725 | 9/1997 | Ward .................................. | 29/888.011 |

*Primary Examiner*—Constantine Hannaher
*Attorney, Agent, or Firm*—Peter H. Kondo

[57] ABSTRACT

Apparatus and process for fabricating an electrostatographic imaging member assembly including providing a hollow electrostatographic drum having a first end and a second end, the first end having a surface selected from the group consisting of an uncoated surface, a surface coated with only a first component of a multiple component adhesive, a surface coated with only a second component for the multiple component adhesive, the second component containing a fluorescent tracer which fluoresces when irradiated with activating radiation, and a surface coated with a mixture of the first component and the second component containing the fluorescent tracer, directing activating radiation at the surface of the first end, detecting the amount of fluorescence emitted from the surface of the first end, and generating a signal which is substantially proportional to the intensity of fluorescence emitted from the surface of the first end, the signal ranging through at least three levels of strength, the first level representing an uncoated surface or a surface coated with only the first component, the second level representing a mixture of the first component and the second component containing the fluorescent tracer, and the third level representing only the second component containing the fluorescent tracer.

15 Claims, 3 Drawing Sheets

MOUNTING ELECTROSTATOGRAPHIC END FLANGE

BACKGROUND OF THE INVENTION

This invention relates in general to a process for fabricating drum and end flange assembly and apparatus for carrying out the process, more specifically, to a process and apparatus for adhesively securing a drum to an end flange.

A photoreceptor conventionally utilized for copiers and printers comprises a hollow electrically conductive metal drum substrate which has been dip coated with various coatings including at least one photoconductive coating comprising pigment particles dispersed in a film-forming binder. These drum type photoreceptors are usually supported on an electrically conductive shaft by drum supporting end flanges (hubs). The hubs are usually constructed of plastic material and have a hole through their center into which a supporting axle shaft is inserted. Generally, at least one of the hubs carries a gear that is either molded in place during formation of the hub or fastened to the hub after the hub is formed. This gear is driven by a powered gear to rotate the drum during image cycling. Since the hubs are usually constructed of electrically insulating plastic material, a suitable electrical grounding means such as a flexible spring metal strip is secured to the hub and positioned to contact both the electrically conductive axle shaft and the electrically conductive metal substrate of the photoreceptor drum to ensure grounding of the drum through the shaft. Various types of grounding means are illustrated in U.S. Pat. No. 4,561,763 and U.S. Pat. No. 5,357,321, the entire disclosures thereof being incorporated herein by reference.

Often the hub or end flange is secured to the end of the drum by a thermoplastic or thermosetting resin adhesive. The use of an adhesive requires a number of manipulation steps and complex equipment to mount a hub to the end of a hollow drum. Solvents may be utilized to apply an adhesive solution to the inside edge of one end of a drum prior to mounting of the hub to the end of the drum. However, safety equipment is required such as solvent recovery systems including large hoods, condensers and other expensive and space consuming equipment to capture the solvent vapors emitted by the adhesive solution during drying. Further, if an adhesive applicator fails to apply an adhesive to the inside edge of one end of a drum, the hub will either fall out after mounting or slip during image cycling. A vision system such as a video camera may be utilized to ensure that the adhesive has, in fact, been applied. However, many adhesives are transparent and difficult to detect visually. A fluorescent tracer material can be added to the adhesive to render it more visible to the video camera. Unfortunately, most solvent adhesives exhibit poor holding strength and can have a short pot life. A short pot live can cause solidification and clogging in the equipment thereby requiring time consuming efforts to clean and remove the solidified adhesive. Failure of hubs to be adhesively secured to a drum ultimately leads to unacceptable copy output. Poor adhesive holding strength and the need for solvent recovery systems can be avoided by replacing solvent adhesives with a solvent free two part epoxy adhesive system. However, a two part epoxy adhesive system comprising a resin (usually about 50 percent by volume) and a curing agent, such as a hardener, (usually about 50 percent by volume) can present a product quality problem in situations where the adhesive appears to have been properly applied to the inside edge of one end of a drum prior to mounting of the hub when, in fact, only the resin or only the curing agent, rather than both, was applied. When only one of the two critical components of an epoxy adhesive has been applied to the inside edge of one end of a drum, the deposited material cannot form a cured epoxy resin adhesive and subsequent installation of the hub into the drum will result in the hub falling out of the end of the drum during packaging or during installation in customer replacement units, or cause the hub to slip in the drum during image cycling in an electrostatographic copier, duplicator or printer. The addition of a fluorescent tracer to either the resin component or the curing agent component of an epoxy resin adhesive facilitates detection of the presence on the inside edge of the drum of only the component containing the fluorescent tracer material. Unfortunately, detection of the presence of only one of the two critical epoxy adhesive components on the inside edge of one end of a drum, does not guarantee that the other component is also present and, therefore, does not solve the problem where the hub falls out of the end of the drum during further processing, during installation in customer replacement units, or failure of the drum-hub assembly to function properly in an electrostatographic copier, duplicator or printer.

Thus, there is a continuing need for improved electrostatographic imaging drum systems in which end flanges are more reliably secured to the drum.

INFORMATION DISCLOSURE STATEMENT

U.S. Pat. No. 5,521,678 issued to Reihle et al on May 28, 1996—An electrostatographic imaging member assembly is disclosed comprising a hollow electrostatographic imaging drum having a first end and a second end, at least one coating on the drum extending from the first end of the drum to the second end of the drum, the coating having an outer electrostatographic imaging surface, drum supporting hubs mounted on the first end of the drum and the second end of the drum, the drum supporting hubs comprising a disk shaped member comprising a disk shaped segment having an exposed annular landing strip surface parallel to and flush with the electrostatographic imaging surface, the annular landing strip surface having a width of at least about 3 millimeters and having an imaginary axis coextensive with an imaginary axis of the drum. The electrostatographic imaging member assembly may be utilized in electrostatographic imaging apparatus in which the hubs support electrostatographic imaging apparatus subassembly components. The electrostatographic imaging member assembly is fabricated by coating the entire external surface of the substrate and mounting the hubs to the ends of the resulting coated substrate. An adhesive may be applied to the outer contacting surface of the hub prior to insertion into one end of the drum.

U.S. Pat. No. 5,357,321 issued to Stenzel et al on Oct. 18, 1994—A drum supporting hub is disclosed comprising a disk shaped member having a circular periphery, a hole extending axially through the center of the disk shaped member, and at least one long thin electrically conductive resilient member secured to the disk shaped member, the resilient member having a central section adjacent the hole and having opposite ends, each of the ends terminating into at least one pointed tip adjacent the circular periphery of the disk shaped member, and the resilient member having a major plane substantially parallel to the axis of the disk shaped member. This hub may be inserted in at least one end of a cylindrical electrostatographic imaging member to produce an imaging member assembly.

U.S. Pat. No. 4,561,763 issued to D. Basch issued on Dec. 31, 1985 a drum supporting hub is disclosed having a tapered pot-like hub configuration comprising a bottom section and a rim, the rim comprising a plurality of circumferentially spaced resilient fingers extending at a slight incline outwardly from the axis of the pot-like hub away from the bottom section, at least three of the fingers having lips at the ends of the fingers, the lips projecting away from the axis for engagement with an end of a cylindrical drum upon insertion of the pot-like hub into the drum, the rim other than the lips having an outside diameter slightly larger than the outside diameter of the bottom. The drum supporting hub is employed in a drum assembly comprising the hub, a cylindrical drum having a circular cross-section and a shaft positioned along the axis of the drum. A metal shim is utilized to electrically ground the drum to the shaft.

SUMMARY OF THE INVENTION

It is, therefore, an object of the present invention to provide improved processes and apparatus for adhesively securing at least one end flange and to an end of a hollow cylindrical member which overcomes the above-noted disadvantages.

It is another object of this invention to provide an improved processes and apparatus for adhesively securing at least one end flange and to an end of a hollow cylindrical member which guarantees detection of the presence of both components of a two part epoxy adhesive.

It is still another object of this invention to provide an improved processes and apparatus for adhesively securing at least one end flange and to an end of a hollow cylindrical member which stops automatic installation of end flanges into ends of drums where inadequate application of adhesive components to the end of drums occurs.

It is yet another object of this invention to provide an improved end flange and hollow cylindrical member assembly which reduces the number of assembly steps utilized to manufacture the assembly.

It is another object of this invention to provide an improved processes and apparatus for adhesively securing at least one end flange and to an end of a hollow cylindrical member which quickly achieves excellent and consistent anchoring of the end flange to the hollow cylindrical member.

It is still another object of this invention to provide an improved processes and apparatus for adhesively securing at least one end flange and to an end of a hollow cylindrical member which guarantees detection of the presence of both components of a two part epoxy adhesive in the proper mix ratio.

The foregoing and other objects of the present invention are accomplished by a process for fabricating an electrostatographic imaging member assembly comprising providing a hollow electrostatographic drum having a first end and a second end, the first end having a surface selected from the group consisting of an uncoated surface, a surface coated with only a first component of for a multiple component adhesive, a surface coated with only a second component for the multiple component adhesive, the second component being containing a fluorescent tracer which fluoresces when irradiated with activating radiation, and a surface coated with a mixture of the first component and the second component containing the fluorescent tracer, directing activating radiation at the surface of the first end, detecting the amount of fluorescence emitted from the surface of the first end, and generating a signal which is substantially proportional to the intensity of fluorescence emitted from the surface of the first end, the signal ranging through at least three levels of strength, the first level representing an uncoated surface or a surface coated with only the first component, the second level representing a mixture of the first component and the second component containing the fluorescent tracer, and the third level representing only the second component containing the fluorescent tracer.

This imaging member assembly is fabricated by apparatus comprising a device for rotating a drum around its axis, the drum having a first end and a second end, a nozzle adapted to form a bead of an multiple component adhesive on at least the first end of the drum, a mixing device adapted to mix at least two components of the multiple component adhesive and deliver the adhesive to the nozzle, only one of the components containing a fluorescent tracer material, a first pump to feed only a first component of the multiple component adhesive to the mixing device, a second pump to feed only a second component of the multiple component adhesive to the mixing device, an activating irradiation source adapted to illuminate the fluorescent tracer whereby the fluorescent tracer fluoresces, and a detector adapted to generate a signal which is substantially proportional to the intensity of fluorescence emitted from the surface of the first end, the signal ranging through at least three levels of strength, the first level representing an uncoated surface or a surface coated with only the first component, the second level representing a mixture of the first component and the second component containing the fluorescent tracer, and the third level representing only the second component containing the fluorescent tracer.

BRIEF DESCRIPTION OF THE DRAWINGS

In general, the advantages of the improved drum supporting end flange and drum assembly, and process and apparatus for fabricating the hub and drum assembly will become apparent upon consideration of the following disclosure of the invention, particularly when taken in conjunction with the accompanying drawings wherein.

These figures merely schematically illustrate the invention and are not intended to indicate relative size and dimensions of actual devices and components thereof.

DETAILED DESCRIPTION OF THE DRAWINGS

The present invention may be employed in any suitable device that requires an end flange to be adhesively attached to a drum. However, for purposes of illustration, the invention will be described with reference to an electrostatographic imaging system. Electrostatographic imaging systems include electrographic imaging systems and electrophotographic imaging systems. A typical electrophotographic imaging system is illustrated in U.S. Pat. No. 3,900,258 to R. F. Hoppner et al, the entire disclosure thereof being incorporated herein by reference.

Figure 1:
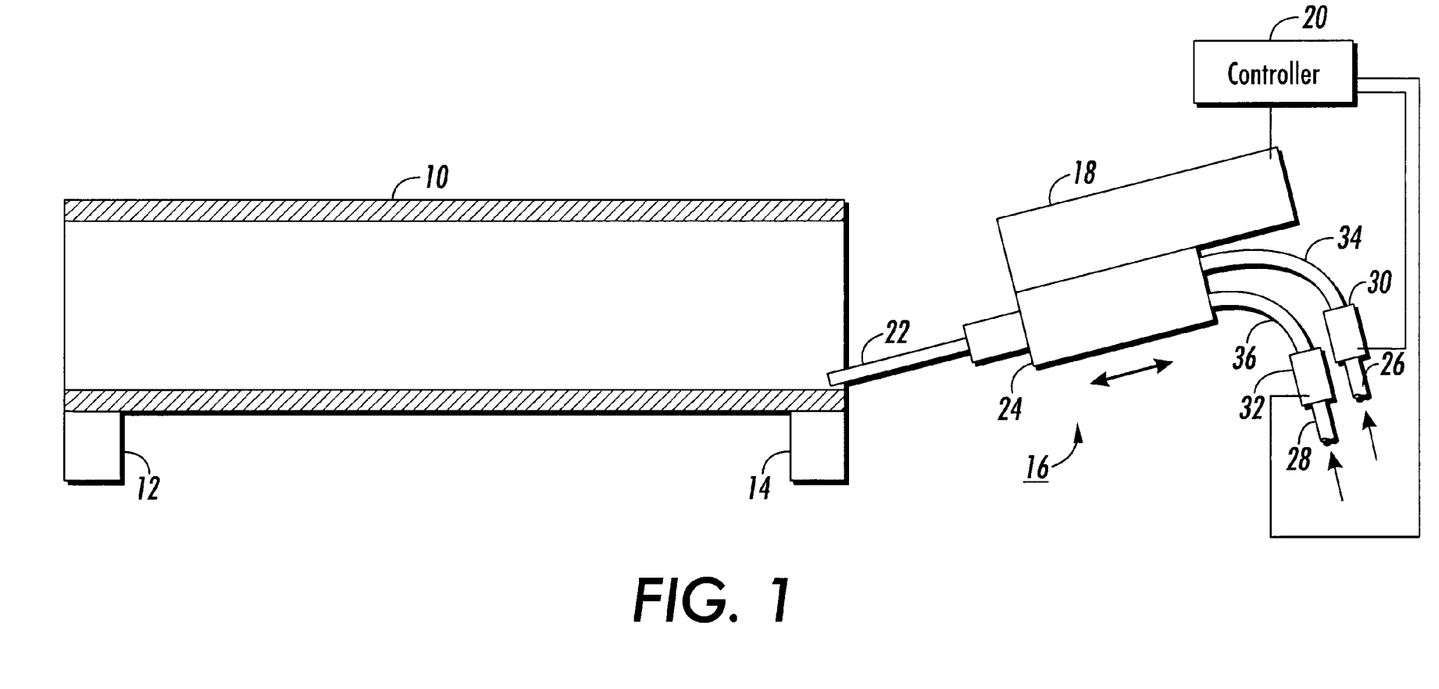
FIG. 1 is a schematic cross sectional side view illustration of a hollow cylindrical member having an interior surface at one end coated with a mixture of a two component adhesive with the aid of a reciprocatable applicator.

Referring to FIG. 1, a hollow electrostatographic drum 10 is shown supported on rotatable roller 12 and rotatable drive roller 14. Adjacent one end of drum 10 is an adhesive applicator 16 which is supported by and reciprocated by a suitable reciprocation device 18 such as a solenoid, two way acting piston, servo motor, and the like. This device advances and retracts the nozzle of adhesive applicator 16 toward and away from the first end of the drum. The reciprocation device 18 may be connected to any suitable programmable logic controller 20 which provides suitable actuator control signals to activate reciprocation device 18 to extend applicator 16 toward or retract applicator 10 away from drum 10. Activation may involve conventional electrical signals from controller 20, or manually, to suitable devices such as solenoid operated valves (not shown) or electrical switches to provide or discontinue providing a positive pressure, a vacuum, ambient air pressure, electricity and the like. Thus, the control functions in the apparatus of this invention are synchronized and integrated with a suitable programmable controller. Expressions such as "activation" and "supplying power" and the like are well known terms intended to include opening and closing solenoid operated valves which can, example, direct compressed gas to appropriate chambers of a two way acting cylinder supporting the applicator 16; activate a solenoid supporting the applicator 16 and the like. Similarly, electrical power to drive electrical equipment such as motors and the like are supplied through suitable wiring and conventional electrical switching. Applicator 16 comprises a nozzle or applicator tube 22 and a mixing housing 24. Mixing housing 24 may comprise any suitable device for mixing at least two liquids together. Typical mixing devices include, for example, static mixers containing baffles, augers and the like. Other mixers include dynamic mixers with rotating blades, and the like. Adhesive material comprising at least two liquid components are separately fed to via at least two hoses 26 and 28 from any suitable storage sources (not shown) with the aid of pumps 30 (e.g. first pump) and 32 (e.g. second pump), respectively, through lines 34 and 36, respectively, to mixing housing 24. Any suitable pumps 30 and 32 may be utilized. Typical pumps include, for example, piston pumps, gear pumps, turbine pumps, and the like. The pumps 30 and 32 may be connected to controller 20 which activates or inactivates the pumps in accordance with a predetermined adhesive application program.

Figure 2:
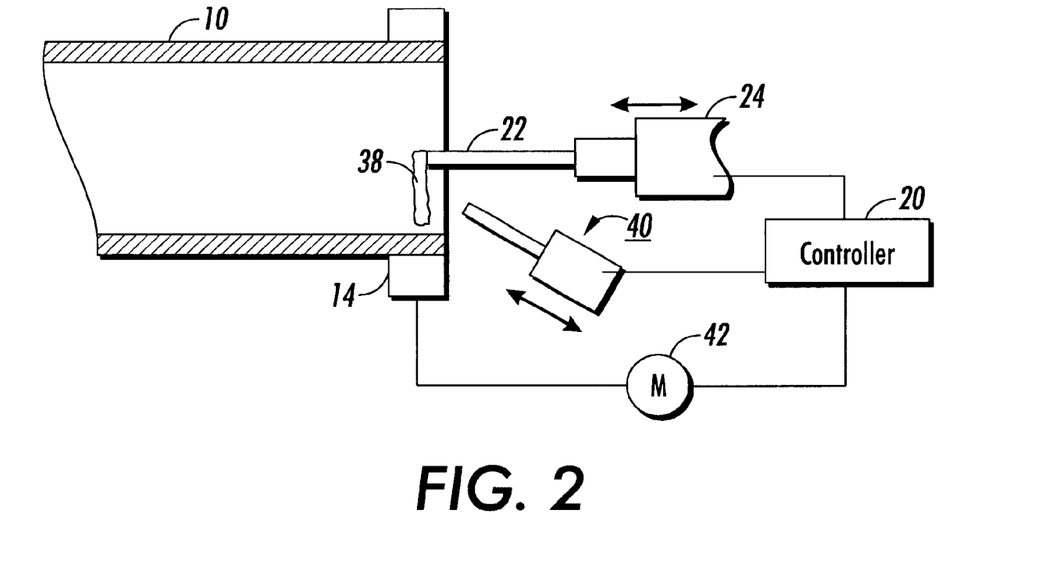
FIG. 2 is a partial schematic cross sectional plan view illustration of the devices shown in FIG. 1 in combination with a reciprocatable camera and radiation source.

Shown in FIG. 2 is a partial plan view of one end of drum 10 and part of applicator 16. An extruded bead of adhesive material 38 is in the process of being applied to the interior surface of one end of drum 10. The bead may be continuous. Also illustrated is a combined activating radiation source and camera 40. Alternatively, the radiation source and camera may be separate devices. Combined radiation source and camera devices are preferred because they are more compact and simpler to mount. Combined radiation source and camera 40 is reciprocated toward and away from drum 10 by any suitable reciprocation device (not shown) similar to the reciprocation device 18 used to reciprocate applicator 16. Drive roller 14 is driven by motor 42. Motor 42 is connected to controller 20 and activated or inactivated by controller 20 in accordance with a predetermined adhesive application program. If desired, the controller can be replaced by ordinary power switches that can be manually activated. If desired, a similar applicator, camera and radiation source may be utilized at the opposite end of drum 10 to apply an adhesive for a second end flange. Application of the adhesive to opposite ends of the drum may be accomplished simultaneously or sequentially. If desired, only one adhesive application station may be utilized for sequentially apply adhesive to opposite ends of drum 10. In this latter embodiment, the drum 10 is usually repositioned 180 degrees after adhesive is applied to a first end so that adhesive can thereafter be applied to the second end. An end flange may be inserted into the first end prior to or subsequent to application of the adhesive to the second end. The adhesive selected should have a sufficiently slow cure rate to avoid complete curing prior to the insertion of the end flanges. If desired a heating device (not shown) such as an oven, hot air blower, induction heater, and the like may be employed to accelerate curing of a deposited adhesive. If the adhesive application system is to be inactive for a time long enough for the mixed components to cure and harden, the mixing housing 24 can be intermittently purged with adhesive or flushed with a suitable material such as a solvent to prevent blocking and to permit reuse upon resumption of the adhesive application process.

Figure 3:
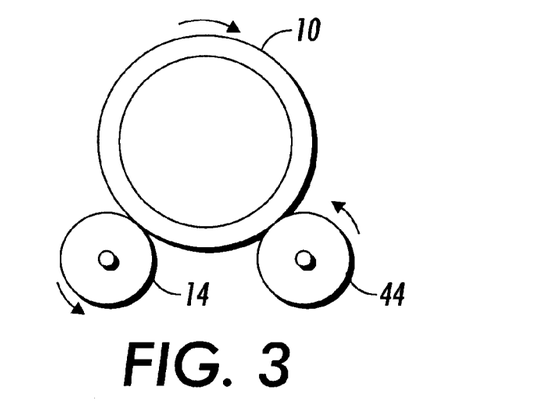
FIG. 3 is a schematic cross sectional end view illustration of the hollow cylindrical member shown in FIGS. 1 and 2 supported for rotation on rollers.

Referring to FIG. 3, drum 10 is supported at one end (first end) by rotatable roller 44 and rotatable drive roller 14. A roller 12 (see FIG. 1) and another rotatable roller (not shown) positioned opposite to roller 44 supports the opposite end (second end) of drum 10. Rotatable drive roller 14 rotates drum 10 around an imaginary axis while the extruded stream of adhesive material 38 (see FIG. 2) is applied to the interior surface of one end of drum 10. Any other suitable device for rotating drum 10 may be utilized. For example, wheels, belts, rollers, and the like.

Figure 4:
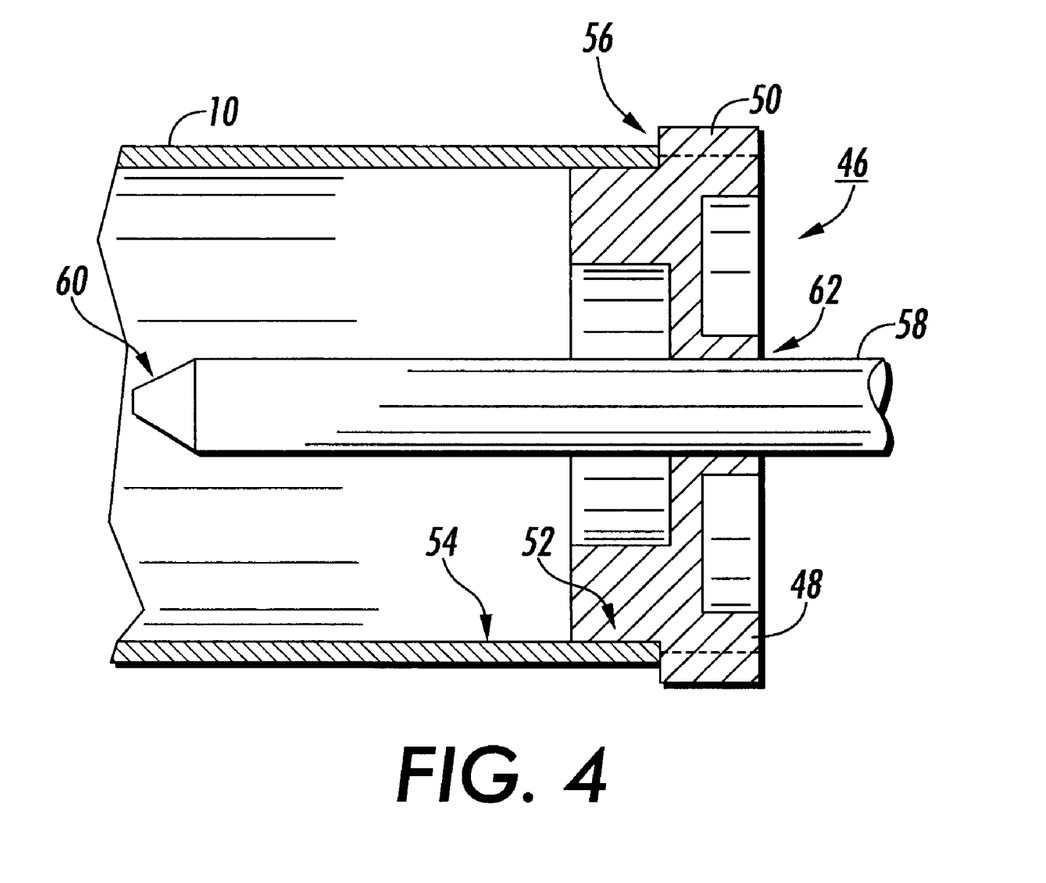
FIG. 4 is a partial schematic cross sectional side view illustration of an end flange mounted in one end of the hollow cylindrical member shown in FIGS. 1, 2 and 3.

In FIG. 4, drum 10 is illustrated with an end flange 46 mounted in one end thereof. Flange 46 comprises a disk shaped member 48 which carries molded gear teeth 50 around the outer periphery thereof. Flange 46 has an arcuate rim 52 which assists in centering end flange 46 in the end of hollow drum 10 so that they are coaxial. Rim 52 may be molded together with disk shaped member 43. If desired, rim 52 and hub 16 can be preformed (not shown) and thereafter fastened to disk shaped member 48 by any suitable means such as by an adhesive, screw, bolts, rivets, or the like. Rim 52 ensures that end flange 46 is centered in the end of drum 10. A slight press or resistance fit of rim 52 of flange 46 into the end of drum 10 may be desirable to prevent easy pull off of end flange 46 and to ensure that end flange 46 is coaxial with drum 10. If desired, the corner edge of rim 52 facing the interior surface of drum 10 may be rounded, tapered, beveled or otherwise inclined toward the drum centerline (not shown) to facilitate insertion of end flange 46 into one end of drum 10 and to promote a snug fit between end flange 46 and drum 10. However, most of the surface to be adhesively attached to the interior surface 54 of drum 10 is preferably parallel to the interior surface 54. Rim 52 may be a continuous rim or a plurality of rim segments such as the ring segments shown in U.S. Pat. No. 4,561,764, the entire disclosure thereof being incorporated herein by reference. In the ring segments embodiment, most or all of the segments contact the adhesive coated drum and the adhesive on the drum that lies opposite intermittent grooves (which are parallel to the drum axis and spaced around rim 52 between the segments) will harden in place and add holding power. Generally, between about 340 degrees of arc and about 360 degrees of arc of the exposed arcuate outer surface of rim 52 should contact and frictionally engage the interior surface 54 of hollow drum 10. A sufficient amount of surface area of rim 52 should be adhesively secured to the interior surface of drum 10 to prevent slippage, i.e. relative motion, between drum 10 and flange 46 when torque is applied to end flange 46 through gear teeth 50. Avoidance of end flange 46 slippage assures registration of electrostatographic images and enhances achievement of quality electrostatographic images. Alternatively, instead of using rim 52 as the main drum contacting surface, a conventional recess (not shown) may be formed in disk shaped member 48 to accept the end of drum 10. Typical physical widths for rim 52 are, for example, between about 0.5 centimeter and about 2 centimeters for a drum 10 having an inside diameter between about 2 centimeters and about 10 centimeters. A shoulder 56 is also provided to maintain the position end flange 46 relative to the end of hollow drum 10. Any suitable supporting shaft 58 may be utilized to support end flange 46. End flange 46, drum 10 and shaft 58 share a common axis. Support shaft 58 may have a pointed end 60 to facilitate insertion of shaft 58 into hole 62. Instead of pointed end 60, shaft 58 may have an end of any other suitable shape. Typical shapes include, for example, pointed ends, rounded ends, flat ends, and the like. The shaft 58 may comprise any suitable material including, for example, metals such as steel, stainless steel, and the like; polymers such as polyesters, polycarbonates, polyamides, and the like; of reinforced polymers such as glass fiber and graphite fiber reinforced plastics, and the like. Generally, a pointed end 60 is preferred for embodiments where a flexible metal spring, shim or the like (not shown) is employed to ground the interior of drum 10 to an electrically conductive shaft 58 by frictional contact. Such grounding springs are well known in the art and described for example in U.S. Pat. No. 5,357,321 and U.S. Pat. No. 4,561,763, the entire disclosure thereof being incorporated herein by reference. The pointed end 60 of shaft 58 deflects the spring to facilitate insertion of the shaft into the end flange and simultaneously ensures that the spring is biased against and frictionally engaged with the shaft for good electrical contact for embodiments where the shaft is electrically conducting and the flange is electrically insulating. End flange 46 may be secured to shaft 58 by any suitable and conventional means (not shown) such as a set screw, key and slot combination, pins, and the like. Alternatively, end flange 46 may be driven directly by hexagonal or square support shafts (not shown) which mate with correspondingly shaped openings (not shown) in end flange 46. The support shaft 58 can be driven directly by an electric motor (not shown), by a belt driven pulley (not shown) attached to shaft 58 or by any other suitable power source as is well known in the art. Alternatively, end flange 46 may freely rotate on support shaft 58. End flange 46 preferably has a circular periphery and a centered hole 62. End flange 46 may be mounted on one end or both ends of drum 10. If mounted on opposite ends of hollow drum 10, the end flanges may have similar or different configurations. Instead of a support shaft which extends through the entire length of the hollow cylindrical member, the end flange 46 may have a molded support shaft stub (not shown) which extends away from the hollow cylindrical member. This latter embodiment preferably utilizes an electrically conductive end flange.

Generally, when utilized to support and drive a hollow electrostatographic imaging drum 10, the adhesively secured end flange 46 of this invention should withstand an applied torque of at least about 30 inch pounds (3.4 N.m) on a 30 mm diameter cylindrical member without encountering slippage between the adhesively secured arcuate surface of the end flange and the adjacent inner surface of the hollow cylindrical imaging member. Where the hollow cylindrical member is driven by torque applied to an end flange located at one end of the cylindrical member and an end flange at the opposite end of the drum is employed to drive numerous other components of an imaging system, the end flanges will be subjected to considerable torque. Also, resistance to cylinder rotation due to peripheral devices such as cleaning blades, brushes or webs in contact with the outer imaging surface of a cylindrical member may need to be considered when determining the amount of torque that must be overcome without slippage between the end flange and the cylinder.

Hollow drum 10 is preferably an electrostatographic imaging drum. Electrostatographic imaging drums comprise a hollow cylindrical electrically conductive substrate and at least one electrostatographic layer. Electrostatographic layers are well known in the art and may comprise a dielectric layer for electrographic imaging or at least one electrophotographic imaging layer for electrophotographic imaging.

In mounting a flange 46 to at least one end of an electrostatographic drum 10, rotation of the drum around the drum axis is initiated by activating motor 42 (see FIG. 2) to drive rotatable drive roller 14 (see FIG. 3). Activation of reciprocation device 18, advances adhesive applicator 16 into position to apply adhesive to the end of drum 10. Activation of pumps 30 and 32 forces at least two components of an adhesive into mixer 18, where the components are blended together, and out of applicator tube 22 onto the moving interior surface of one end of drum 10 to form an extruded bead of adhesive material 38 (see FIG. 2). One of the adhesive components contains a fluorescent tracer material prior to mixing in mixer 18. Combined radiation source and camera (detector) 40 is advanced toward the region where the extruded bead of adhesive material 38 is being deposited and both the radiation source and camera components are activated. When struck by the activating radiation, the fluorescent component originally in one of the components of the adhesive fluoresces and emits radiation having a wavelength that is different from the radiation from the radiation source in combined radiation source and camera 40. The application of the adhesive is monitored using the camera component of the combined radiation source and camera 40, which is sensitive to the radiation wavelength or wavelength range emitted when the fluorescent tracer material is exposed to a source of activating radiation such as ultraviolet (UV) radiation. The camera component detects the radiation emitted from the fluorescing bead of adhesive material 38 and generates an output signal (e.g., current output), the strength of which varies with the intensity of the radiation from the fluorescing bead of adhesive material 38. The output signal from the camera is sent to controller 20 where it is compared to a predetermined benchmark range representing a desirable mix of both the resin and curing agent components. A typical combined radiation source and camera is an ultraviolet camera Model No. E65UV20-02, available from Cutler Hammer Corporation which emits a UV source and detects fluorescence. The output range for the Model No. E65UV20-02 is 0–20 mA (milliampere) depending upon the intensity of fluorescence detected by the camera. If the final deposited adhesive is selected is to contain two components in the correct proportions of 50 percent by weight of each component (i.e., 1 part by weight of each), a mid scale range reading, e.g. 8–12 mA, can be set as the benchmark detection range for acceptable deposits and the adhesive coated drum can be allowed to progress to the next processing station, e.g., a station where an end flange 16 is robotically or manually pressed onto the coated end of the drum prior to complete curing of the deposited adhesive. If no adhesive is applied, there is no output signal from the camera during the time period when the adhesive is supposed to be applied by applicator 16, and an alarm is activated by controller 20. If only the adhesive component free of the fluorescent material is applied, there is no signal from the camera and an alarm or other suitable signal such as assembly line shut down, flashing lights, various combinations thereof, and the like are activated by controller 20. If only the component of the adhesive component containing the fluorescent material is applied to the end of the drum, there is a high output signal, e.g. 16–20 mA, from the camera and an alarm and/or other signal is activated by controller 20. Since it is critical that the presence of the correct proportion of both components of the adhesive actually be applied and detected, a detector that has an signal output range must be used. The predetermined benchmark signal range will vary depending upon many factors such as the signal output range capabilities of the camera, the proportions of resin and curing agent needed for acceptable curing of the particular multicomponent adhesive, type of fluorescent material, amount of fluorescent tracer material, transparency of the adhesive components, intensity of activating radiation, and the like actually selected. Thus, the predetermined benchmark signal range is normally initially determined experimentally for the specific materials and equipment used. For example, any suitable camera may be utilized having an output range sufficient for distinguishing the absence of one or both adhesive components from presence of both adhesive components for the specific fluorescent material selected. Preferably, the adhesive fluoresces in the visible light band. Where desired, a photodiode or any other suitable radiation detector which detects fluorescence in the visible light band may be substituted for a camera. The photodiode or other suitable radiation detector should have a signal output range which varies with the amount of fluorescence emitted by the deposited adhesive, i.e., which provides an electrical signal representative of the amount of radiation detected. Generally, a camera is preferred because it is not bothered by stray or background light. When the mixture of adhesive components in the correct proportions has been applied to the drum and a mid scale camera output reading is detected, the photoreceptor progresses to the next processing station. Although a camera system that can provide a mid scale reading for the presence of both components of the adhesive, some latitude is available where the presence of both components of the adhesive is indicated by a signal that is closer to the lower end or upper end of the camera output range where, for example, one wishes to use equipment on hand or changes materials in the process. Thus, for example, in the case where a camera with a different output range is utilized (e.g., 0–40 mA) and the camera is calibrated for 0 output when no tracer is in the component and 20 mA for 100 percent tracer component, then the correct 50/50 mix output would be approximately 10 mA. In any event, the signal strength range should be sufficiently broad to allow detection of the presence of both components in the deposited adhesive.

The application of the adhesive components to the hollow drum ends can be monitored with a camera mounted inside of large diameter tubes. However, however, if the interior contains objects that obstruct view such as silencers or if the drum has a small diameter, positioning of a camera in the interior may be difficult or impossible.

Preferably, controller 20 is a self-contained, dedicated minicomputer. Controller 20 coordinates the operation of the various components. In particular, controller 20 responds to a sensor such as the camera component in the combined radiation source and camera 40 or other suitable sensor (e.g. a signal photodiode) and provides suitable actuator control signals to the adhesive pumps, drive motors and the like employed to apply adhesive components and to monitor the effectiveness of the process. The controller 20 may include an expert system including various logic routines to analyze sensed parameters in a systematic manner and reach conclusions on the state of the machine.

Any suitable activating radiation, such as ultraviolet, having a wavelength to which the fluorescent tracers are sensitive may be utilized for determining the presence or absence of the adhesive components. A typical activating beam emitted from the radiation source utilized in the process of this invention has a wavelength between about 300 nm and about 400 nm. Preferably, the UV radiation beam has a wavelength of between about 340 nm and about 360 nm. The radiation source should emit radiation of sufficient intensity to cause the deposited tracer material to fluoresce when exposed to the radiation.

The adhesive material comprises at least two components such as a resin and a curing agent. Preferably, the deposited adhesive material is free of any solvent. Typical multicomponent adhesive materials include, epoxies, urethanes, acrylics, and the like. A preferred adhesive are epoxies. Epoxies can be monomers or prepolymers that further react with curing agents to yield a thermosetting polymer. Epoxy resins are characterized by the presence of a three-membered cyclic ether group referred to as an epoxy group, 1,2-epoxide, or oxirane. Preferred epoxy resins are diglycidyl ethers of bisphenol A derived from bisphenol A and epichlorohydrin. In addition to bisphenol, other polyols such as aliphatic glycols and novolacs may be used to produce epoxy resins. Epoxy resins may also include compounds based on aliphatic and cycloaliphatic backbones. The epoxy resins, prior to curing, range from low viscosity liquids to solid meltable resins. Typical curing agents to convert epoxy resin to a thermoset resin includes, for example, anhydrides, amines, polyamides, Lewis acids, and the like. Examples of hardener type curing agents for bisphenol A epoxy resins include, short-chain aliphatic polyamines such as diethylentriamine and triethylenetetramine; oxylalkylated short-change polyamines such as $H_2NC_2H_4NHC_2H_4NHCH_2CH_2OH$ and $HOCH_2CH_2NHC_2H_4NHC_2H_4NHCH_2CH_2OH$; long-chain polyamine adducts such as trimethyl-1,6-hexanediamine and polyaminoamide, and the like. The mixing ratios for the bisphenol A epoxy resins and hardeners can range about 100 to about 10 to 100 to about 60, by weight, depending on the specific materials selected. Other epoxy resins that may be mixed with hardeners include, for example, epoxy phenol novolac resins with hardeners such as aromatic amines, catalytic curing agents, phenolics and anhydrides. If desired, mixture of epoxy resins may be utilized. A typical mixture includes, for example, triglycidyl-p-aminophenol resins mixed a bisphenol A-epoxy resin. Curing agents that are catalytic, initiate resin homopolymerization, either cationic or anionic, using a Lewis acid or base in the curing process. The Lewis acid catalysts can be a complex such borontrifluoride with amines or ethers. Curing agents that are co-reactive are polyfunctional reagents that are employed in stoichometric quantities. Typical classes of co-reactive curing agents include, for example, polyamines, polyaminoamides, polyphenols, polymeric thiols, polycarboxylic acids and anhydrides, and the like. Preferably, curing of the epoxy resins involves a liquid epoxy resin as cured via the epoxy groups at room temperature with nonaromatic amines and at slightly elevated temperatures with aromatic amines. Epoxy resins and curing agents for the epoxy resins are commercially available from companies such Celanese, Ciba-Geigy, The Dow Chemical Company, Reichold Chemicals, Shell Chemical Company, and Union Carbide Corporation. For room temperature curing systems, hardeners such as polyamides, aminoamides and aliphatic-amines are preferred. Typical curing agents include, for example, aliphatic amines such as diethylenetriamine, triethylenetetramine, and the like; aromatic amines such as meta-phenylenediamine, methylenedianiline, diaminodiphenylsulfone, and the like; catalytic curing agents such as piperidene, boron trifluoride-ethylamine complex, benzyldimethylamine, and the like; acid anhydrides such as acidic methyl anhydride, dodecenylsuccinic anhydride, hexahydrophthalic anhydride, alkendic anhydride, and the like. Generally, room temperature curing adhesives are preferred to conserve energy and for heat sensitive electrophotographic imaging members. However, heat may be used, if desired, particularly where faster curing is desired.

Luminescence is broadly defined as the emission of electromagnetic radiation in excess of thermal radiation. Luminescent materials are called phosphors. Phosphors are generally prepared as powders and contain one or more impurity ions or activators present in 1:5 mol percent. There are many types of luminescent materials, some of which require a special source of excitation such as ultraviolet radiation. Daylight-fluorescent pigments, in contrast, require no artificially generated energy. Daylight, or an equivalent white light can excite these materials not only to reflect colored light selectively, but to give off an extra glow of fluorescent light, often with high efficiency and surprising brilliance. A preferred excitation source for the ultraviolet fluorescent phosphors utilized in the process and apparatus of this invention includes ultraviolet radiation.

A fluorescent substance is one that absorbs radiant energy of certain wavelengths and, after a fleeting instant, gives off part of the absorbed energy as quanta of longer wavelengths. In contrast to ordinary colors in which the absorbed energy degrades entirely to heat, light emitted from a fluorescent color adds to the light return by simple reflection to give the extra glow characteristics of a daylight-fluorescent material or ultraviolet fluorescent material (when bathed in ultraviolet light).

Luminescent pigments are based largely on zinc sulfide and zinc-cadmium sulfide which are doped with an activating material, e.g., silver, copper, manganese, to the extent of about 0.033 to about 1.0 weight percent. Depending on the activator, under UV radiation a wide spectrum of colors can be obtained, e.g., blue, green, yellow, orange and red. Generally, the detector utilized should readily detect the increased intensity of wavelength or wavelength band emitted when the fluorescent material is struck by activating radiation. Any suitable amount of fluorescent material be utilized so long as it radiates at a level which can be detected by a sensor sensitive to the wavelength or wavelength band that is given off. Ultraviolet fluorescent material and ultraviolet radiation are preferred for optimum detection.

Any suitable end flange 46 may be utilized for the adhesively secured drum-flange assembly of this invention. Flange 46 may comprise any suitable metal, plastic or combination of a metal and a plastic materials. Although more expensive, typical metals include, for example, steel, aluminum, copper, bronze, brass and the like. Typical plastic materials include thermosetting or thermoplastic resins which are dimensionally stable. These plastic members may be filled or unfilled. Any suitable conventional filling material may be utilized. Typical thermoplastic resins include, for example, acrylonitrile butadiene styrenes (ABS), polycarbonates, nylons, acrylics and the like. Typical thermosetting resins include, for example, alkyds, allylics, epoxies, phenolics, and the like. Plastic end flanges are preferred because they are easily molded and are less expensive. If desired, plastic end flanges may comprise electrically conductive components such as conductive filler particles of metal, carbon black or the like to impart electrical conductivity properties to the end flange.

It is clear that the product and process of this invention provides a consistent and reliable system which leads to positive identification of the components of a deposited multiple component adhesive.

The invention will now be described in detail with respect to specific preferred embodiments thereof, it being noted that these examples are intended to be illustrative only and are not intended to limit the scope of the present invention. Parts and percentages are by weight unless otherwise indicated.

EXAMPLE I

A hollow photoreceptor drum coated with a charge generating layer and a charge transport layer was placed on 4 rotatable support rollers similar to that illustrated in FIGS. 1 and 3. The drum had a length of 34 centimeters, a diameter of 30 millimeters and a coating thickness of 24 micrometers. Rotation of the drum around the drum axis was initiated by activating an electric motor to drive one of the rotatable support rollers. A two way acting pneumatic cylinder was activated to advance an adhesive applicator into position to apply adhesive to the inside edge of one end of the drum. A pair of piston pumps were activated to simultaneously force one part by weight of a resin (Lord 305-1, available from Lord Corporation, Erie Pa.) from one supply source and one part by weight of a hardener (Lord 305-2, also available from Lord Corporation) from a separate supply source into a baffled static mixer where the resin and hardener components are thoroughly blended together. The hardener contained a sufficient concentration of fluorescent particles to fluoresce when the hardener was combined with the resin and the combination was illuminated by a UV light source. After blending, the mixture of resin, hardener and fluorescent material (blended adhesive material) exited out of the static mixer through a nozzle tube onto the moving interior surface at one end of the drum to form an extruded bead of blended adhesive material. A combination ultraviolet radiation source and fluorescence detecting camera (Model No. E65UV20-02, available from Cutler Hammer Corporation) was positioned adjacent the nozzle tube to bathe the adhesive bead being deposited in ultraviolet light. When struck by the activating UV radiation, the fluorescent component in the adhesive fluoresced and emitted radiation having a wavelength of 600 nm that was detected by the camera. The output range for the Model No. E65UV20-02 was 0 mA to 20 mA (milliampere). depending upon the intensity of fluorescence detected by the camera. Since the final deposited adhesive was selected to contain the two components in the correct proportions of 50 percent by weight of each component (i.e., 1 part by weight of each), a mid scale range reading, e.g. 8–12 mA, was set as the benchmark detection range for acceptable deposits of blended adhesive components. The output signal from the camera was sent to a programmable controller (PLC-5, available from Allen—Bradley Division of Rockwell Industries) where it was compared to the predetermined benchmark. The programmable controller was also programmed to control the electric motor driving one of the rotatable support rollers, the valves for the two way acting pneumatic cylinder and gear pumps so that the drum was rotated one revolution while the piston pumps forced the blended adhesive components out of the nozzle tube to form a bead that extended 350 degrees around the inner surface of one end of the drum. Since the deposited adhesive was an acceptable blend, the camera output reading of the fluorescence emitted by the UV irradiated adhesive bead was 10 mA and the adhesive coated drum end was allowed to progress to the next processing station where an end flange was pressed onto the coated end of the drum prior to complete curing of the deposited adhesive.

EXAMPLE II

The process described in Example I was repeated, except that the piston pumps were not activated whereas the drum was rotated and the camera and UV light source were activated. Since no adhesive was applied, there was no output current signal from the camera during the time period when the adhesive was supposed to be applied by the applicator. The controller detected the absence of an output current signal and activated an alarm. Similarly, when only the adhesive component free of the fluorescent material was applied, there was no current signal from the camera and an alarm was activated by the controller.

EXAMPLE III

The process described in Example I was repeated, except that only the component of the adhesive component containing the fluorescent material, i.e. only the hardener was applied to the end of the drum because the piston pump for the resin was not activated during the drum coating operation. The high output signal from the camera to the controller was a 18 mA and the controller activated an alarm.

The invention has been described in detail with particular reference to preferred embodiments thereof but it will be understood that variations and modifications can be effected within the spirit and scope of the invention as described herein above and as defined in the appended claims.

What is claimed is:

1. A process for fabricating an electrostatographic imaging member assembly comprising
   providing a hollow electrostatographic drum having a first end and a second end, the first end having a surface selected from the group consisting of
   an uncoated surface,
   a surface coated with only a first component of for a multiple component adhesive,
   a surface coated with only a second component for the multiple component adhesive, the second component being containing a fluorescent tracer which fluoresces when irradiated with activating radiation, and
   a surface coated with a mixture of the first component and the second component containing the fluorescent tracer,
   directing activating radiation at the surface of the first end,
   detecting the amount of fluorescence emitted from the surface of the first end, and generating a signal which is substantially proportional to the intensity of fluorescence emitted from the surface of the first end, the signal ranging through at least three levels of strength, the first level representing an uncoated surface or a surface coated with only the first component, the second level representing a mixture of the first component and the second component containing the fluorescent tracer, and the third level representing only the second component containing the fluorescent tracer.

2. A process according to claim 1 wherein the adhesive is an epoxy adhesive.

3. A process according to claim 1 wherein the second component is a resin.

4. A process according to claim 1 wherein the second component is a curing agent.

5. A process according to claim 4 wherein the curing agent is a hardener.

6. A process according to claim 4 wherein the curing agent is a catalyst.

7. A process according to claim 1 including mounting an end flange to the first end when the signal strength is the second level representing a mixture of the first component and the second component containing the fluorescent tracer.

8. A process according to claim 1 including repeating the steps employed for the first end to the second end.

9. Apparatus for fabricating an electrostatographic imaging member assembly comprising
   a device for rotating a drum around its axis, the drum having a first end and a second end,
   a nozzle adapted to form a bead of an multiple component adhesive on at least the first end of the drum,
   a mixing device adapted to mix at least two components of the multiple component adhesive and deliver the adhesive to the nozzle, only one of the components containing a fluorescent tracer material,
   a first pump to feed only a first component of the multiple component adhesive to the mixing device,
   a second pump to feed only a second component of the multiple component adhesive to the mixing device,
   an activating radiation source adapted to illuminate the fluorescent tracer whereby the fluorescent tracer fluoresces,
   a detector adapted to generate a signal which is substantially proportional to the intensity of fluorescence emitted from the surface of the first end, the signal ranging through at least three levels of strength, the first level representing an uncoated surface or a surface coated with only the first component, the second level representing a mixture of the first component and the second component containing the fluorescent tracer, and the third level representing only the second component containing the fluorescent tracer.

10. Apparatus according to claim 9 including a controller to activate and inactivate the device for rotating the drum, the first pump,
    the second pump,
    the radiation source, and
    the detector.

11. Apparatus according to claim 9 including a device to advance and retract the nozzle toward and away from the first end of the drum.

12. Apparatus according to claim 9 wherein the irradiation source is adapted to emit ultraviolet radiation.

13. Apparatus according to claim 9 wherein the detector is a camera.

14. Apparatus according to claim 9 including a controller adapted to compare the signal strength of the signal from the detector to benchmarks corresponding to the at least three levels.

15. Apparatus according to claim 14 wherein the controller is adapted to activate an alarm when the signal strength corresponds to the first level or third level.

* * * * *